United States Patent [19]

Dattagupta et al.

[11] Patent Number: 5,587,472
[45] Date of Patent: Dec. 24, 1996

[54] COUMARIN-LABELED NUCLEOSIDE 5'-TRIPHOSPHATES

[75] Inventors: Nanibhushan Dattagupta, San Diego, Calif.; Jürgen Köcher, West Haven, Conn.

[73] Assignee: Bayer Corporation, Tarrytown, N.Y.

[21] Appl. No.: 460,027

[22] Filed: Jun. 2, 1995

Related U.S. Application Data

[63] Continuation of Ser. No. 799,470, Nov. 26, 1991, abandoned, which is a continuation-in-part of Ser. No. 744,555, Aug. 13, 1991, abandoned.

[51] Int. Cl.$^6$ .......... C07H 19/10; C07H 19/20; C07H 21/04
[52] U.S. Cl. .......... 536/26.2; 536/24.31; 536/24.32
[58] Field of Search .......... 536/24.31, 24.32, 536/26.2

[56] References Cited

U.S. PATENT DOCUMENTS

| | | | |
|---|---|---|---|
| 4,472,301 | 9/1984 | Buckler et al. | 435/7.4 |
| 4,617,261 | 10/1986 | Sheldon, III et al. | 435/6 |
| 4,711,955 | 12/1987 | Ward et al. | 536/29 |
| 4,828,979 | 5/1989 | Klevan | 435/6 |
| 4,857,455 | 8/1989 | Khanna et al. | 435/7 |
| 4,948,882 | 8/1990 | Ruth | 536/27 |
| 5,015,733 | 5/1991 | Smith et al. | 536/23 |
| 5,026,840 | 6/1991 | Dattagupta et al. | 536/27 |
| 5,124,247 | 6/1992 | Ansorge | 435/6 |
| 5,300,656 | 4/1994 | Kuckert et al. | 549/288 |

FOREIGN PATENT DOCUMENTS

| | | |
|---|---|---|
| 2030243 | 5/1991 | Canada . |
| 0063879 | 3/1982 | European Pat. Off. . |
| 0429907 | 11/1990 | European Pat. Off. . |
| 4026613 | 2/1992 | Germany . |

OTHER PUBLICATIONS

Nucleosides & Nucleotides, 8 (5&6), pp. 1161–1163 (1989).
Nucleic Acids Research, vol. 18, No. 19, pp. 5843–5851 (1990).
Proc. Nat. Acad. Sci. USA, vol. 71, No. 9, pp. 3537–3541 (1974).
Archives of Biochemistry and Biophysics 178, pp. 8–18, (1977).
Analytical Biochemistry, 177, pp. 85–89, (1989).
Langer et al., Proc. Natl. Acad. Sci., 78(11): 6633–6637, 1981.
Chemical Abstracts, vol. 114, 1991, Columbus, Ohio, US; abstract No. 185914q, S. V. Chekalin et al. 'Laser Fentosecond MPI Mass Spectroscopy of Dye–Labeled Nucleotides.', p. 835; col. 1.
IEEE J. Quantum Electron. vol. 26, No. 12, 1990, pp. 2158–2161.

Chemical Abstracts Formula Index, vol. 114, 1991, Formulas C24–Z p. 3298F, formula C24H28N709PS; *Adenosine, 5'(S–(2–((2–((4–methyl–2–oxo–2 H–1–benopyran–7–yl)amino)ethyl)amino)–2–oxoethyl) hydrogen phosphorothioate), (133395–32–1), 185914q *Guanosine, 5'–(S–(2–((2–((4–methyl–2–oxo–oxoethyl) hydrogen phosphorothioate), (133395–33–2), 1895914q*.

*Primary Examiner*—Gary L. Kunz
*Attorney, Agent, or Firm*—Sprung Horn Kramer & Woods

[57] ABSTRACT

A fluorescent label compound having the formula $$A—B^1—B^2—B^3—C$$

wherein

A represents the residue of a natural or synthetic nucleotide or nucleoside or a derivative thereof;

$B^1$ represents a divalent spacer radical or a single bond;

$B^2$ represents a divalent spacer radical;

$B^3$ represents a divalent spacer radical or a single bond; and

C represents a coumarin radical having the formula

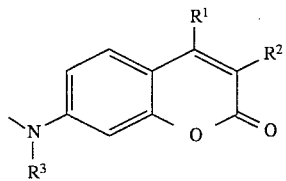

in which $R^1$ represents hydrogen or cyano;

$R^2$ represents phenyl or thiazolyl bonded in the 2-, 4- or 5-position, wherein the phenyl is unsubstituted or substituted by nitro, cyano, amino, $—NH—C_{1-4}$-alkyl, $—(CH_2)_{1-4}—NH_2$, $—(CH_2)_{1-4}—NH—(CH_2)_{1-3}—CH_3$, carboxy, $C_{1-4}$-alkoxycarbonyl, $C_{1-4}$-alkoxycarbonyloxy, hydroxy, $C_{1-4}$-alkylaminocarbonyl, or $C_{1-4}$-alkylcarbonylamino and either further unsubstituted or substituted by $C_{1-4}$-alkyl, fluorine, chlorine or bromine, and where the thiazolyl is unsubstituted or monosubstituted or disubstituted by chlorine, cyano, carboxyl, or $C_{1-4}$-alkoxycarbonyl, or the thiazolyl is fused in the 4- and 5-position with a benzene ring which is either unsubstituted or substituted by carboxyl, amino, or hydroxyl;

$R^3$ represents hydrogen, $C_{1-4}$-alkyl, $C_{1-4}$-alkoxycarbonyl-$C_{1-4}$-alkyl, or phenylsulphonyl, where the $C_{1-4}$-alkyl is unsubstituted or substituted by hydroxyl, amino, carboxyl, or $C_{1-4}$-alkoxycarbonyl, and where the phenylsulphonyl is unsubstituted or monosubstituted or disubstituted by chlorine, bromine, or $C_{1-4}$-alkyl;

or where one of the radicals $R^2$ or $R^3$ denotes or is substituted by a primary or secondary amino group, hydroxyl, carboxyl, or $C_{1-4}$-alkoxycarbonyl, or can be converted into such a group by hydrolysis or hydrogenation.

5 Claims, No Drawings

COUMARIN-LABELED NUCLEOSIDE 5'-TRIPHOSPHATES

This application is a continuation of application Ser. No. 07/799,470, filed Nov. 26, 1991, now abandoned, which application is a continuation-in-part of U.S. application Ser. No. 07/744,555 filed Aug. 13, 1991, now abandoned.

BACKGROUND OF THE INVENTION

1. Field of the Invention

The present invention relates to a novel fluorescent label compound, which can be enzymatically incorporated into a nucleic acid. The labeled nucleic acid can be used to detect the presence of a DNA or RNA sequence of interest in a sample nucleic acid.

2. Description of the Related Art

The technique of hybridization of a labeled oligonucleotide to a sample DNA to afford sequence-specific nucleic acid detection has become a powerful tool in analytical molecular biology. Initially, labeling was accomplished mainly with radioactive isotopes. However, radioactive labeled probes typically have the disadvantage of instability, low resolution, and all the pitfalls of handling radioisotopes. In order to circumvent labeling with radioactive isotopes, a number of methods have been recently developed for non-radioactive labeling and detection.

For example, K. Mühlegger et al., "Synthesis and Use of New Digoxigenin-Labeled Nucleotides in Non-Radioactive Labeling and Detection-Labeled Nucleic Acids", *Nucleosides & Nucleotides*, 8 (5 & 6), pp. 1161–1163 (1989), describe the chemical synthesis and incorporation into DNA of novel digoxigenin-derivatized 5-aminoallyl-2'-deoxyuridine-5'-triphosphates. Hybridization and subsequent detection by ELISA technique allows the detection of homologous DNA down to 0.1 pg.

Hans-Joachim Höltke et al., "Non-Radioactive Labeling of RNA Transcripts In Vitro with the Hapten Digoxigenin (DIG); Hybridization and ELISA-Based Detection", *Nucleic Acids Research*, 18 (19), pp. 5843–5851 (1990), describe an alternative method for labeling nucleic acid probes with the cardenolide digoxigenin. However, the detection of digoxigenin disadvantageously requires a secondary reagent, such as an antibody linked to an enzyme.

EP-A2-63879 describes chemically stable new nucleotide derivatives that contain biotin, imino-biotin, lipoic acid and other determinants attached covalently to the pyrimidine or purine ring and their synthesis. These compounds will interact specifically and uniquely with proteins such as avidin or antibodies. This can be utilized for the detection and localization of nucleic acid components.

U.S. Pat. No. 4,617,261 discloses non-radioactive labeling reagents consisting of an alkylating intercalation moiety, such as a psoralen moiety, a divalent linker, and a monovalent label moiety, like biotin. These reagents are used to label nucleic acids.

Finally, Dirks et al., *Experimental Cell Research*, 194, pp. 310–315 (1991), describe the use of fluorescein-, digoxigenin- and biotin -(di)deoxyXTPs and terminal deoxynucleotidyl transferase for small scale labeling of synthetic oligonucleotides for use as probes in the in situ detection of multiple RNA sequences. Apparently, Boehringer Mannheim has now made available fluorescein-12 -dUTP for this purpose. See, *BM Biochemica*, 8 (5), p. 15 (September 1991).

Despite these known methods, there continues to exist a need for labels for nucleic acids which are easy to obtain, easy to incorporate into nucleic acid probes, and easy to detect.

SUMMARY OF THE INVENTION

To meet this need there has now been developed a novel fluorescent label compound having the formula $$A—B^1—B^2—B^3—C$$

wherein

A represents the residue of a natural or synthetic nucleotide or nucleoside or a derivative thereof;

$B^1$ represents a divalent spacer radical or a single bond;

$B^2$ represents a divalent spacer radical;

$B^3$ represents a divalent spacer radical or a single bond; and

C represents a coumarin radical having the formula

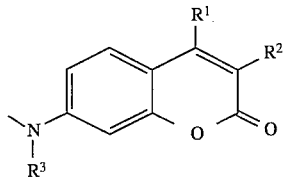

in which $R^1$ represents hydrogen or cyano;

$R^2$ represents phenyl or thiazolyl bonded in the 2-, 4- or 5-position, wherein the phenyl is unsubstituted or substituted by nitro, cyano, amino, —NH—$C_{1-4}$-alkyl, —$(CH_2)_{1-4}$—$NH_2$, —$(CH_2)_{1-34}$—NH—$(CH_2)_{1-3}$—$CH_3$, carboxy, $C_{1-4}$-alkoxycarbonyl, $C_{1-4}$-alkoxycarbonyloxy, hydroxy, $C_{1-4}$-alkylaminocarbonyl, or $C_{1-4}$-alkylcarbonylamino and either further unsubstituted or substituted by $C_{1-4}$-alkyl, fluorine, chlorine or bromine, and where the thiazolyl is unsubstituted or monosubstituted or disubstituted by chlorine, cyano, carboxyl, or $C_{1-4}$-alkoxycarbonyl, or the thiazolyl is fused in the 4- and 5-position with a benzene ring which is either unsubstituted or substituted by carboxyl, amino, or hydroxyl;

$R^3$ represents hydrogen, $C_{1-4}$-alkyl, $C_{1-4}$-alkoxycarbonyl-$C_{1-4}$-alkyl, or phenylsulphonyl, where the $C_{1-4}$-alkyl is unsubstituted or substituted by hydroxyl, amino, carboxyl, or $C_{1-4}$-alkoxycarbonyl, and where the phenylsulphonyl is unsubstituted or monosubstituted or disubstituted by chlorine, obromine, or $C_{1-4}$-alkyl;

it also being possible that one of the radicals $R^2$ or $R^3$ denotes or is substituted by a primary or secondary amino group, hydroxyl, carboxyl, or $C_{1-4}$-alkoxycarbonyl, or can be converted into such a group by hydrolysis or hydrogenation.

Because the novel fluorescent label compound comprises the residue of a natural or synthetic nucleotide or nucleoside or a derivative thereof, the novel fluorescent label can be easily incorporated into nucleic acids enzymatically using enzymes such as terminal transferase and DNA and RNA polymerases. (The use of DNA or RNA polymerases will usually require a primer and template according to the conventional methods). Moreover, because the novel fluorescent label compound also comprises a coumarin fluorescent dyestuff residue, the novel fluorescent label fluoresces, thereby giving a visual signal indicative of the presence in a nucleic acid sample of a nucleic acid sequence of interest.

The invention, thus, also comprises a test for the presence of a particular nucleic acid sequence in a sample, wherein the sample is subjected to a labeled probe under hybridizing conditions and the sample is thereafter assayed for hybridization product, the improvement wherein the probe is labeled with the novel fluorescent label compound.

The invention further comprises a diagnostic test kit for use in the detection of a particular nucleic acid sequence in a sample, the kit comprising the novel fluorescent label compound.

DETAILED DESCRIPTION OF THE INVENTION

In the novel fluorescent label compound having the forementioned formula, the residue A preferably represents the residue of a natural or synthetic nucleotide selected from the group consisting of AMP, ADP, ATP, GMP, GDP, GTP, CMP, CDP, CTP, UMP, UDP, UTP, TMP, TDP, TTP, 2Me AMP, 2Me ADP, 2Me ATP, 1Me GMP, 1Me GDP, 1Me GTP, 5Me CMP, 5Me CDP, 5Me CTP, 5MeO CMP, 5MeO CDP, 5MeO CTP, deoxy-, dideoxy-nucleotides thereof, and other derivatives thereof.

$B^1$, $B^2$ and $B^3$ preferably independently or collectively represent a spacer chain of up to about 50 atoms selected from carbon, hydrogen, oxygen, nitrogen, and sulfur, it also being possible for $B^1$ or $B^3$ to represent a single bond. More particularly, $B^1$, $B^2$ and $B^3$ independently or collectively represent a spacer chain of about 2–20 atoms selected from carbon, hydrogen, oxygen, nitrogen, and sulfur, it also being possible for $B^1$ or $B^3$ to represent a single bond.

For example, such spacer has a chain length between the radicals A and C of up to about 50 atoms, not taking into account the possibility of branches. Such spacer may be the polyfunctional radical of a peptide; hydrocarbon, such as an alkylene, an alkenylene, an alkynylene, an arylene, and substituted derivatives thereof; polyalcohol; polyalkoxide; polyether; polyamine; polyimine; carbohydrate, $-C=CH-CH_2-NH-$; $-glycyl-glycyl-glycyl-$; $-NH(CH_2)_5-CO-$; the radical of spermine; the radical of spermidine; $-NH-(CH_2)_6-NH-$; or $-NH-CH_2-CH_2-NH-$; $-CH=CH-CH_2-NH-CO-(CH_2)_5-NH-CO-(CH_2)_3-$; $-NH-(CH_2)_6-NH-CO-(CH_2)_5-NH-CO-(CH_2)_3-$.

The coumarin radical is preferably selected from among those having the forementioned formula wherein $R^2$ represents phenyl or thiazolyl bonded in the 2-, 4- or 5-position, where phenyl is unsubstituted or substituted by carboxyl, $C_{1-4}$-alkylcarbonyloxy, amino, $-NH-C_{1-4}$-alkyl, $-(CH_2)_{1-4}-NH_2$, $C_{1-4}$-alkyl, cyano, fluorine, chlorine, or bromine, and where thiazolyl is unsubstituted or substituted by chlorine, cyano, or carboxyl, or the thiazolyl is fused in the 4- and 5-position with a benzene ring which is either unsubstituted or substituted by carboxyl or amino; $R^3$ represents hydrogen, methyl, ethyl, $-(CH_2)_{1-4}-OH$, $-(CH_2)_{1-4}-NH_2$, or $-(CH_2)_{1-4}-COOH$; it also being possible that one of the radicals $R^2$ and $R^3$ denotes or is substituted by a primary or secondary amino group, hydroxyl, carboxyl, or $C_{1-2}$-alkoxycarbonyl.

Particularly preferred are coumarin radicals having the forementioned formula, wherein $R^2$ represents phenyl or thiazolyl bonded in the 2-position, where phenyl is unsubstituted or substituted by para-carboxyl, para-amino, para-$NH$-$C_{1-4}$-alkyl, para-$CH_2-NH_2$, cyano, methyl, or ethyl, and where thiazolyl is unsubstituted or substituted by chlorine, cyano, or carboxyl, or the thiazolyl is fused in the 4-and 5-position with a benzene ring which is either unsubstituted or substituted by carboxyl or amino; it also being possible that one of the radicals $R^2$ and $R^3$ denotes or is substituted by a primary or secondary amino group, hydroxyl, or carboxyl.

Preferably, as an example, the fluorescent label compound is the compound having the formula:

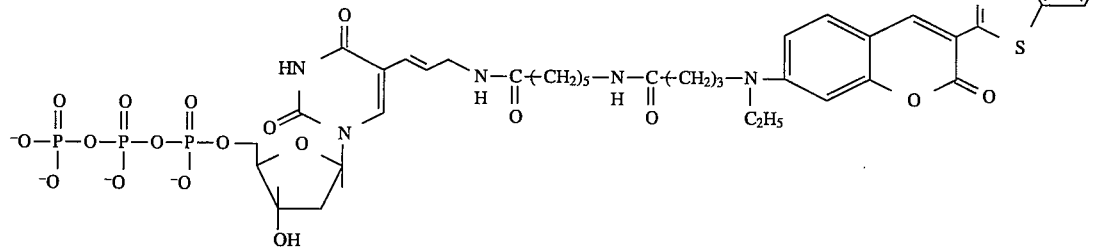

or the compound having the formula

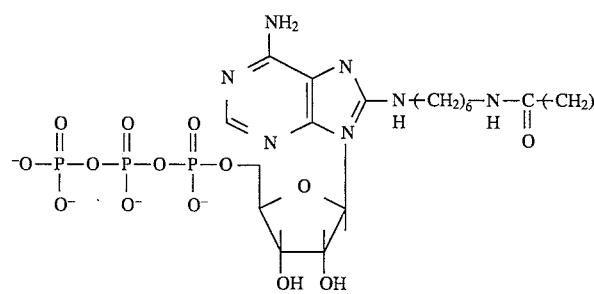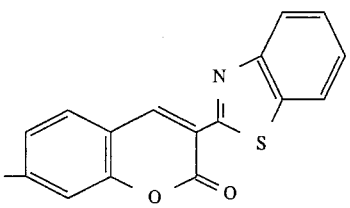

The novel fluorescent label compounds can be prepared by any of a number of well known methods of preparation. In general, they will be "built" from the coumarin dyestuff component and the nucleotide or nucleoside component, both of which will possess a site that can be derivatized. The derivatizable sites on the two components will then be chemically linked by the spacer.

For example, the novel fluorescent label compounds according to the present invention can be prepared as follows:

(1) reacting a compound of the formula A—Z with a compound of the formula L—$B^{11}$—M to form A—$B^1$—H wherein Z represents e.g., hydrogen or bromine, L represents a reactive double bond or an amino group, M represents an amino group. The product obtained will have the formula A—C=C—$B^{11}$—NR—H or A—NR—$B^{11}$—NR—H, wherein R represents hydrogen, alkyl, or phenyl, the moieties —C=C—$B^{11}$—NHR— and —NHR—$B^{11}$—NHR— constituting $B^1$; or (2) if $B^1$ is a single bond, reacting the compound A—Z with a compound of the formula V—$B^{22}$—W to form A—$B^1$—$B^2$—H, wherein V represents —COOR, R represents $C_{1-4}$-alkyl, and W for example represents amino. In this instance, the product obtained has the formula A—CO—$B^{22}$—NR—H, wherein R represents hydrogen, alkyl, or phenyl, and the moiety —CO—$B^{22}$—NR— represents the combination —$B^1$—$B^2$—; then (3) if $B^3$ is not a single bond, reacting a compound of the formula C—Q with a compound of the formula X—$B^{33}$—Y to form C—$B^3$—OR, wherein Q represents, e.g., hydrogen, X represents COOR', R' represents $C_{1-4}$-alkyl, and Y represents halogen, e.g., Br. In this instance, the product obtained has the formula C—$B^{33}$—COOR, the moiety —$B^{33}$—CO— constituting $B^3$; then (4) reacting the product of step (1) with V—$B^{22}$—W and then with the product of step (3) or, if $B^3$ is a single bond, with C—Q; or (5) reacting the product of step (2) with the product of step 3 or, if $B^3$ is a single bond, with C—Q.

See, e.g., P. R. Langer et al., Proc. Natl. Acad. Sci. USA, 78, 6633 (1981); DE 4,026,613; and H. Heitzmann and F. M. Richards, Proc. Natl. Acad. Sci. USA, 71, p. 3537 (1974).

The coumarin compounds of the formula C—Q can be prepared by (a) reacting an m-aminophenol of the formula

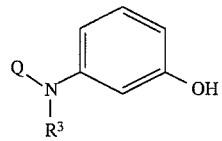

in which $R^3$ and Q have the forementioned meanings, with a formylacetic acid derivative of the formula

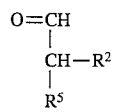

in which $R^2$ has the forementioned meaning and $R^5$ represents cyano, $C_{1-4}$-alkoxycarbonyl, or carboxyl;

provided that wherein if $R^5$=CN, first an imino derivative of the formula

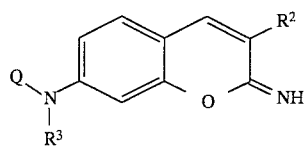

is formed and this imino derivative is hydrolyzed with elimination of the imino group; or (b) reacting a salicylaldehyde of the formula

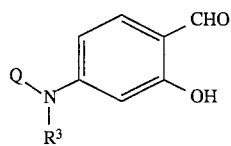

in which $R^3$ and Q have the forementioned meanings with an acetic acid derivative of the formula

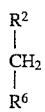

in which $R^2$ has the forementioned meaning and $R^6$ represents cyano, $C_{1-4}$-alkoxycarbonyl, or carboxyl;

provided that wherein if $R^6$=CN, first an imino derivative of the formula

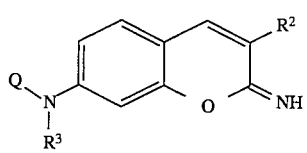

is formed and this imino derivative is hydrolyzed with elimination of the imino group; or (c) in the case where $R^1$ denotes cyano, the intermediate or product in (a) and (b) is reacted with cyanide ions to give the imino-cyano intermediate of the formula

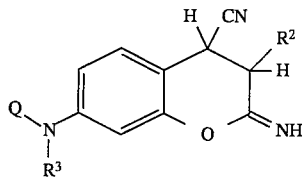

or the cyano intermediate of the formula

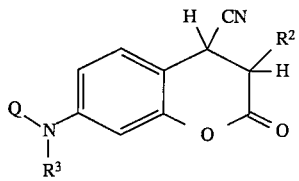

wherein in each $R^2$, $R^3$ and Q have the forementioned meanings and this intermediate is oxidized to the cyanocoumarin derivative and optionally additionally hydrolyzed.

Details of process parameters for the preparation of the coumarin starting materials are detailed in U.S. Ser. No. 07/610,864, the disclosure of which is incorporated herein by reference.

The starting materials L—$B^{11}$—M, V—$B^{22}$—W, and X—$B^{33}$—Y are very well known products.

The starting materials, A—Z, are well-known to those of ordinary skill in the art and are commercially available.

The novel fluorescent label compounds according to the present invention can be incorporated into nucleic acids using techniques well-known to those of ordinary skill in the art. For example, if desired, the novel fluorescent label compound could be incorporated into a nucleic acid sequence by subjecting the probe sequence to the novel fluorescent label compound in the presence of terminal transferase. The novel fluorescent label compound should thereby be incorporated at the end of the then existing nucleic acid probe sequence and without the requirement for a template.

Such labeled nucleic acid probe can be Used to detect the presence of a nucleic acid sequence of interest in a nucleic acid sample. The labeled nucleic acid is applicable to all conventional hybridization assay formats and, in general, to any format that is possible based on formation of a hybridization product or aggregate comprising the labeled nucleic acid. Such formats are well-known to those of ordinary skill in the art.

Like other coumarin dyestuffs, the novel fluorescent label compounds according to the present invention are strong dyes and possess excellent light fastness properties. As such, nucleic acids labeled with the novel fluorescent label compound according to the invention can be usually detected visually and at low concentration.

The present invention will now be described with reference to the following non-limiting examples.

EXAMPLE 1: Preparation of compound 3

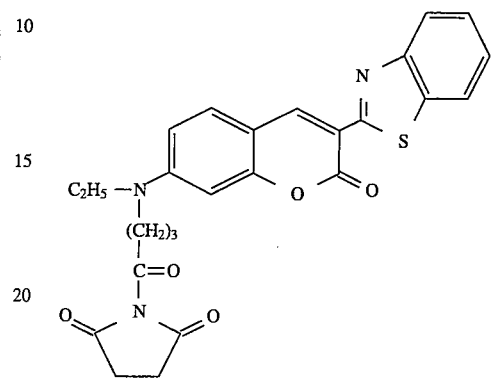

Compound 2 has been prepared by converting the corresponding carboxylic acid 1

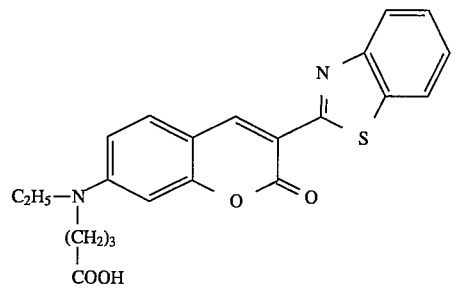

by known methods, as it is already described for the activation of biotin, see e.g. H. Heitzmann and F. M. Richards, *Proc. Natl. Acad. Sci. USA*, 71, 3537 (1974). The carboxylic acid and its preparation has been described in the patent application DE 4026613.

A solution of 500 mg 6-aminocaproic acid ($3.45 \times 10^{-3}$ mol) in 3 ml $H_2O$, adjusted to pH 9 with 0.1 m $Na_2CO_3$, is added to a solution of 50 mg of compound 2 ($10^{-4}$ mol) in 50 ml DMF at room temperature. A yellow material precipitates immediately. The reaction mixture is stirred for 5 hours at room temperature. Thin layer chromatography (TLC) indicates that the desired reaction has occurred (Toluene/Methanol 5:4, Silicagel).

compound 1: $r_f$ (retention factor)=0.90 compound 1 after the hydrolysis of the NHS-ester: $r_f$=0.29 new product compound 3: $r_f$=0.25

The reaction mixture is evaporated to dryness under vacuum, and 15 ml $H_2O$ is added to the remaining yellow residue. The formed suspension is adjusted to pH=1 with 8 N HCl and centrifuged. The supernatant, which is almost colorless, is removed, and another 15 ml of $H_2O$ is added to resuspend the precipitate. The suspension is centrifuged and the supernatant removed. After thorough vacuum drying of the precipitate, the yield of compound 3 having the formula

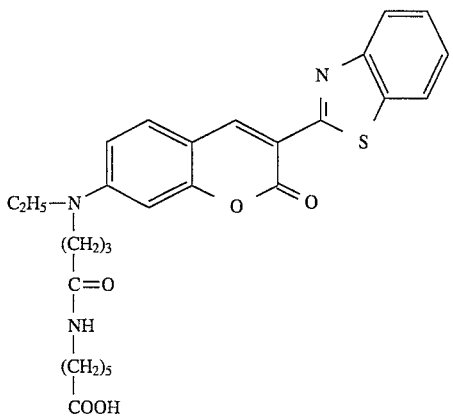

is 43 mg (83%).

EXAMPLE 2: Preparation of compound 6

15.8 mg of compound 3 ($3 \times 10^{-5}$ mol) and 5 mg N-Hydroxysuccinimide ($5.05 \times 10^{-5}$ mol) are dissolved in 3 ml DMF. To this solution, 10.7 mg Dicyclohexylcarbodiimide ($5.19 \times 10^{-5}$ mol), dissolved in 2 ml DMF, is added. The mixture is stirred at room temperature for about 7 hours, additional 27 mg solid N-Hydroxysuccinimide ($2.7 \times 10^{-4}$ mol) and 53 mg solid Dicyclohexylcarbodiimide ($2.57 \times 10^{-4}$) mol are added to the reaction solution. After stirring for additional 17 hours most of the carboxylic acid 3 has been converted to the N-Hydroxysuccinimide ester 4 having the formula

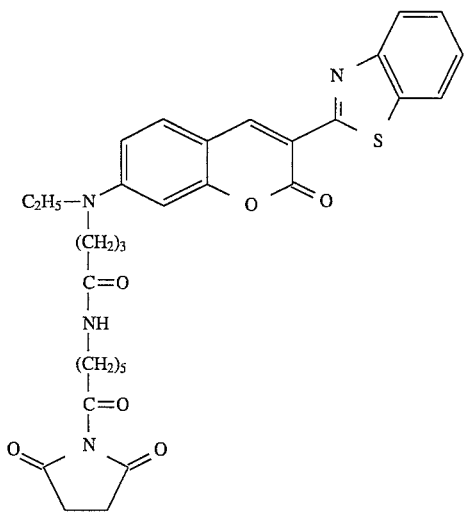

according to TLC (Toluene/Methanol 5:4, Silicagel, $r_f$ of new compound 4 - 0.83).

A solution of 4.9 mg 5-allylamino-dUTP (compound 5 having the formula

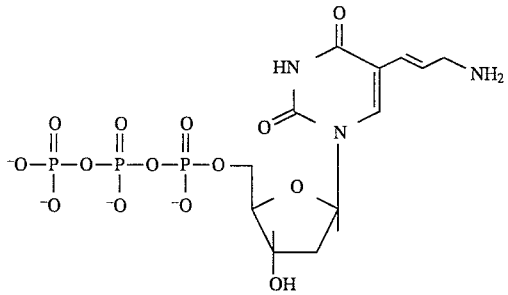

$8 \times 10^{-6}$ mol), which is prepared according to P. R. Langer et al., Proc. Natl. Acad. Sci. USA 78, 6633 (1981), in 7 ml $H_2O$ is adjusted to pH=9.4 with 0.1M $Na_2CO_3$. The reaction mixture containing the activated compound 4 (see above) is added to the 5-allylamino-dUTP-solution at room temperature. A yellow material precipitates immediately. TLC can detect the new fluorescing nucleotide (t-BuOH 3.5/acetone 2.5/ conc. $NH_3$/1.5 HOAc 1.5/$H_2O$ 1, cellulose, $r_f$=0.72.)

The suspension is stirred for 4.5 hours at room temperature and evaporated to dryness under vacuum. Consecutive chromatography of the residue on a Sephadex G 10 column (Pharmacia) with $H_2O$ as eluent gives 1.4 mg of the compound 6 (16%), having the formula

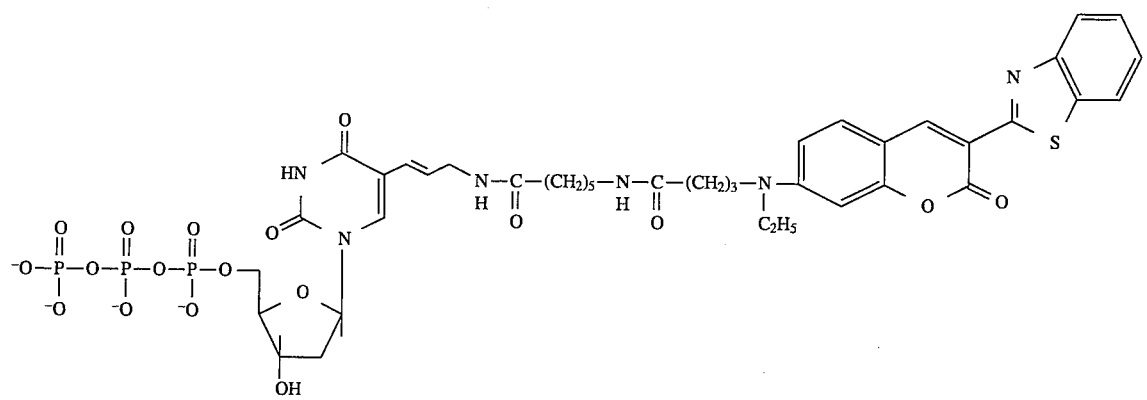

EXAMPLE 3: Incorporation of compound 6 into an 18 mer oligonucleotide by the enzyme terminal deoxynucleotidyl transferase The fluorescing nucleotide 6 is incorporated into an 18 mer oligonucleotide (sequence: CTC TAT TGA TTA CCA TGA) by terminal deoxynucleotidyl transferase (Boehringer Mannheim) as follows: 5.9 µg 18 mer oligonucleotide (synthesized in an Applied Biosystems Inc. (Foster City, Calif.)'s automated oligonucleotide synthesizer using their reagents) and 140 µg compound 6 were dissolved in a reaction buffer containing 140 mmol/l K-cacodylate, mmol/l Tris-buffer pH 7.6 1 mmol/l $CoCl_2$ and 0.1 mmol/l dithiothreitol (DTT) (total volume 50 µl). Enzymatic incorporation was achieved by addition of 21 U terminal deoxynucleotidyl transferase and incubation for 19 hours at 37° C.

20% denaturing polyacrylamide gel electrophoresis (57 V/cm, 1 hour, buffer: 90 mM tris-borate, 1 mM EDTA, pH 8, at room temperature) showed a fluorescent DNA band which can already be detected visually.

Electrophoresis of the same control mixture without incubation at 37° C. results in no detectable fluorescent DNA. This indicates that the new fluorescent nucleotide 6 is covalently incorporated into the oligonucleotide and not just nonspecifically bound to it.

Ethidium bromide staining also indicates that an elongation of the oligonucleotide has occurred.

EXAMPLE 4: Incorporation of compound 6 into a hairpin oligonucleotide by the Klenow fragment of DNA polymerase 5 µl 5 × reaction buffer (containing 650 mmol/l potassium phosphate pH=7.4, 32.5 mmol/l $MgCl_2$, 5 mmol/l DTT and 160 µg/ml BSA) and 5 µl of a 5 × nucleosidetriphosphate mixture (containing 2.5 mmol/l of dATP, dCTP, dGTP and the fluorescing nucleotide 6 instead of dTTP) are combined with 2 µg of a 69 mer hairpin oligonucleotide (sequence: AGATTTTCTAGATTTCATCTTCCTC-CCTATAGTGAGTCGTATTATTTTTTT-TAATACGACTCACT ATAG, synthesis as described in example 3) and 5.5 U of Klenow fragment of DNA polymerase (total volume 25 µl). The mixture is incubated at 37° C. for 50 minutes. 20% denaturing polyacrylamide gel electrophoresis (experimental conditions see example 3) of the reaction mixture indicates that incorporation of the fluorescing nucleotide 6 has occurred because a fluorescent DNA band is visible. Gel electrophoresis of the same mixture but without the enzyme does not result in a fluorescent band. This indicates that the fluorescent nucleotide 6 is covalently incorporated into the DNA and not nonspecifically bound.

EXAMPLE 5: Fluorescent nucleotides (comparison)

The following combinations of different nucleoside triphosphates and fluorescent dyes have been synthesized.

—fluoresceine attached to 5-allylamino-dUTP (compound 7)

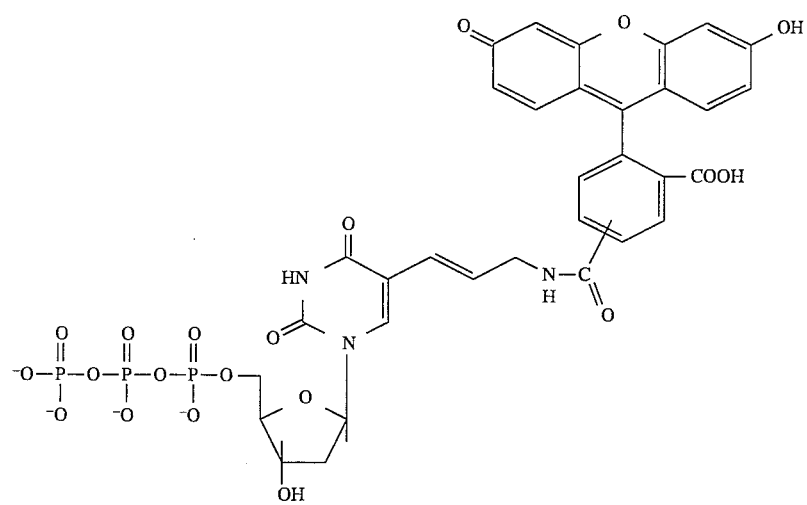
—fluorescamine derivative attached to 5-allylamino-dUTP (compound 8)
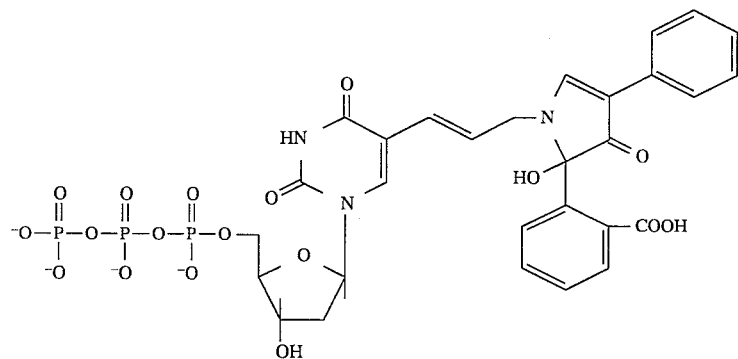
—fluoresceine derivative attached to 8-(6-aminohexylamino)-dATP (compound 9)
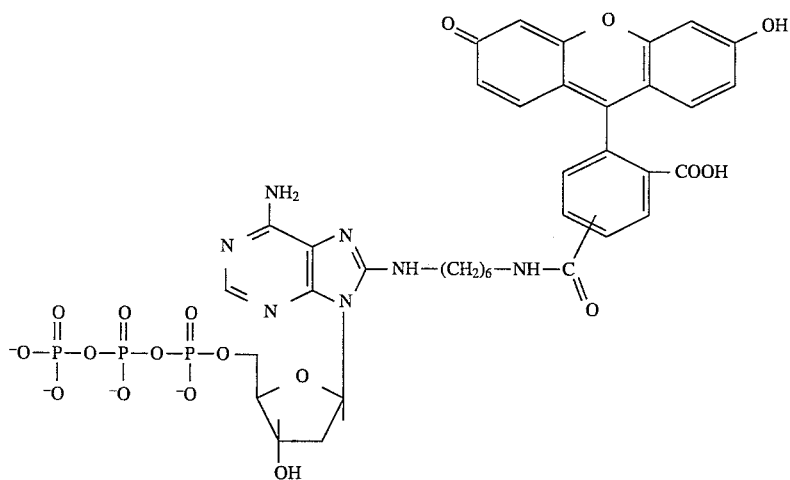
—fluorescamine derivative attached to 8-(6-aminohexylamino)-dATP (compound 10)

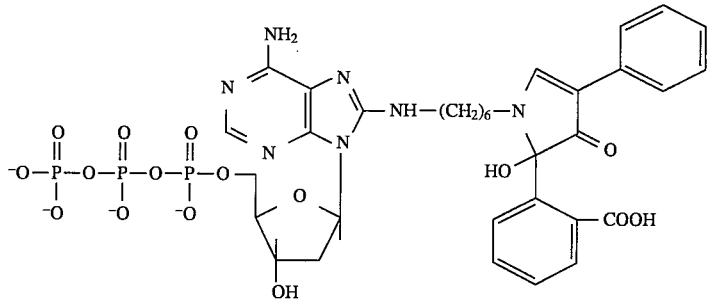

—fluorescamine derivative attached to 8-(6-aminohexy-lamino)-ATP (compound 11)

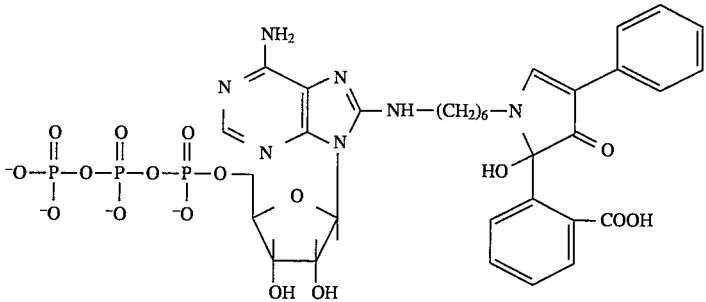

Fluorescamine was purchased from Aldrich (Milwaukee, Wis.), NHS-fluoresceine (5- and 6- isomer mixture) from Molecular Probes (Eugene, Oreg.) and 8-(6-aminohexylamino)-ATP from Sigma (St. Louis, Mo.).

5-Allylamino-dUTP is obtained as described above and 8-(6-amino hexylamino)-dATP is synthesized according to a procedure published by C. -Y. Lee et al., Arch. Biochem. Biophys. 178, 8 (1977). The coupling of the amino group containing nucleotides to fluorescamine (20 fold excess compared to the nucleotide) is done in a mixture of acetone and 0.1 M $Na_2CO_3$ pH 10 at room temperature. After proving by TLC that the reaction is complete, the reaction mixture is evaporated to dryness under vacuum, and the residue is chromatographed on Sephadex G 10 (Pharmacia) with water as eluent.

The coupling of NHS-fluoresceine to the nucleotides is done in $Na_2CO_3$-solution (pH 9–9.5). The purification is done in the same way as described for the fluorescamine-conjugates.

The experiments described in example 3 are repeated with the above mentioned fluorescing nucleotides. The results of the experiments with these nucleotides 7–11 indicate no detectable incorporation of fluorescent moiety into an oligonucleotide by terminal deoxynucleotidyl transferase as it was described for the fluorescing nucleotide 6 in example 3.

Under the same conditions, 5-allylamino-dUTP can be incorporated 5–10 times, and 8-(6-aminohexylamino)-ATP is incorporable 1–2 times into an oligonucleotide.

The experiment with compound 7 has been reinvestigated using different concentrations. It has been found that this compound is also acceptable to terminal deoxynucleotidyl transferase and can be incorporated into a single-stranded oligonucleotide as is described in example 3. Important for a successful experiment is the right concentration of compound 7 in the reaction mixture. It could be shown that the incorporation rate is higher at relatively low concentrations (smaller than 0.5 mmol/l), while higher concentrations of the nucleotide 7 result in decreasing or non-detectable incorporation.

EXAMPLE 6: Use of the product of example 4 for hybridization

The oligonucleotide described in example 4 can form a partial double stranded structure before incorporation of any fluorescent dNTPs. The single stranded part of the molecule is a specific sequence of major outer membrane protein of chlamydia trachomitis.

The genomic DNA sample from chlamydia trachomitis is denatured in 0.5 M NaOH and spotted onto a strip of nitrocellulose paper (Schleicher & Schuell, Inc. Keene, N.H., U.S.A.). The paper is then soaked and rinsed in an aqueous solution of 0.5 M Tris-HCl (pH 7.5) containing 1.5M NaCl. The paper is then dried in a vacuum oven for 4 hours at 80° C. The paper is then prehybridized with the product of example 4 following a procedure described by Dattagupta et al., Analytical Biochemistry, 177, 85 (1989). After hybridization fluorescence is detected either visually using a hand held lamp or photographed in a similar fashion as polyacrylamide gels. Appearance of fluorescence at the sample DNA spot is an indication of positive results.

EXAMPLE 7: Preparation of compound 13

11.6 mg of compound 3 ($2.2\times10^{-5}$ mol), 22.6 mg 1-(3-dimethylaminopropyl)-3-ethylcarbodimide methiodide ($7.6\times10^{-5}$ mol) and 16.2 mg N-hydroxysulfosuccinimide (sodium salt, $7.5\times10^{-5}$ mol) in 1 ml DMF are heated to 50° C. for 7.5 hours. According to TLC (toluene/ethanol 5:4, silicagel) most of the carboxylic acid 3 has been converted to the N-hydroxysulfosuccininimide ester 12 having the formula

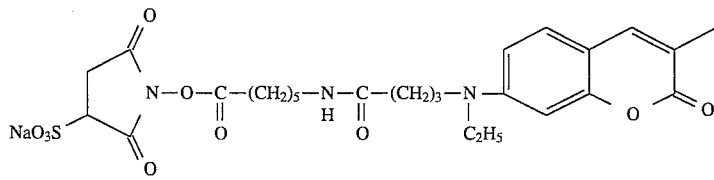

The reaction mixture is cooled to room temperature and a solution of 8-(6-aminohexyl) aminoadenosine-5'-triphosphate (Li-salt, sigma, $10^{-5}$ mol) in 100 µl $H_2O$ and 20 µl pyridine ($2.5 \times 10^{-4}$ mol) is added. After stirring at room temperature overnight only traces of a new compound are detectable. The mixture is then sonicated for 3 hours, 2 mg of 4-dimethylaminopyridine ($1.6 \times 10^{-5}$) is added and the mixture is sonicated for an additional 5 hours. According to TLC (t-BuOH 3.5/acetone 2.5/conc. $NH_3$ 1.5/HOAc 1.5/ $H_2O$, cellulose, $r_f$=0.72) a new product is now easily detectable. The reaction mixture is evaporated to dryness under vacuum. Chromatography of the residue (3 times) on a Sephadex G 10 column (Pharmacia) with water as eluent gives 3.5 mg of the compound 13 (29%), having the formula Ethidium bromide staining also indicates that an elongation of the oligonucleotide has occurred.

No incorporation can be detected if the concentration of compound 13 in the labelling mixture is increased 5–10 times.

EXAMPLE 9: Incorporation of compound 13 into RNA transcripts by T7 RNA polymerase RNA transcripts containing the fluorescent ribonucleotide 13 are obtained according to a method described in the European Patent Applications EP 427073 and EP 427074:

5 µl 5× transcription buffer (containing 200 mmol/l Tris-buffer pH 8, 50 mmol/l $MgCl_2$, 50 mmol/l NaCl,

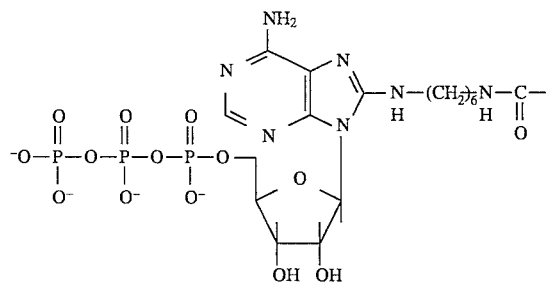

EXAMPLE 8: Incorporation of compound 13 into an 18 mer oligonucleotide by the enzyme terminal deoxynucleotidyl transferase The fluorescent ribonucleotide 13 is incorporated into an 18 mer oligonucleotide (sequence: CTC TAT TGA TTA CCA TGA) by terminal deoxynucleotidyl transferase (Pharmacia) as follows:

1.8 µg 18 mer oligonucleotide (synthesized in an Applied Biosystems Inc.'s (Foster City, Calif.) automated oligonucleotide synthesizer using their reagents) and 2.5 µg compound 13 were dissolved in a reaction buffer containing 140 mmol/l K-cacodylate, 30 mmol/l Tris-buffer pH 7.6, 1 mmol/l $CoCl_2$ and 0.1 mmol/l dithiothreitol (DTT) (total volume 50 µl). Enzymatic elongation was achieved by addition of 22 U terminal deoxynucleotidyl transferase and incubation for 16.5 hours at 37° C.

20% denaturing polyacrylamide gel electrophoresis (experimental conditions see example 3) shows a fluorescent DNA band which can be detected visually.

5 mmol/l dithiothreitol (DTT) and 350 µg/ml BSA), 5 µl of a 5 × ribonucleoside triphosphate mixture (containing 2.5 mmol/l CTP, GTP and UTP and the fluorescing compound 13 instead of ATP), RNA guard (Pharmacia, 36 U) and $^{32}$P-UTP (10 µCi) are combined with 100 pg of a 69 mer hairpin oligonucleotide (sequence as described in example 4) and 67 U of T7 RNA polymerase (Pharmacia (total volume 25 µl)). The mixture is incubated at 37° C. for 3 hours. 20% denaturing polyacrylamide gel electrophoresis (experimental conditions see example 3) and subsequent autoradiography can detect RNA molecules.

It will be appreciated that the instant specification and claims are set forth by way of illustration and not limitation and that various modifications and changes may be made without departure from the spirit and scope of the present invention.

What is claimed is:

1. A fluorescent label compound having the formula:

A—B$^1$—B$^2$—B$^3$—C wherein

A represents a radical selected from the group consisting of dATP-8-yl and dUTP-5-yl;

B$^1$—B$^2$—B$^3$ collectively represent a spacer moiety selected from the group consisting of:

—CH=CH—CH$_2$—NH—CO—(CH$_2$)$_5$—NH—CO—(CH$_2$)$_3$—a and

—NH—(CH$_2$)$_6$—NH—CO—(CH$_2$)$_5$—NH—CO—(CH$_2$)$_3$—a wherein

"a" represents the point of attachment to A; and

C represents a coumarin radical having the formula:

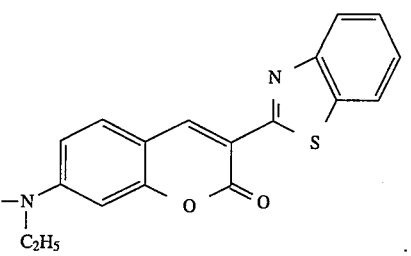

2. The fluorescent compound according to claim 1 having the formula

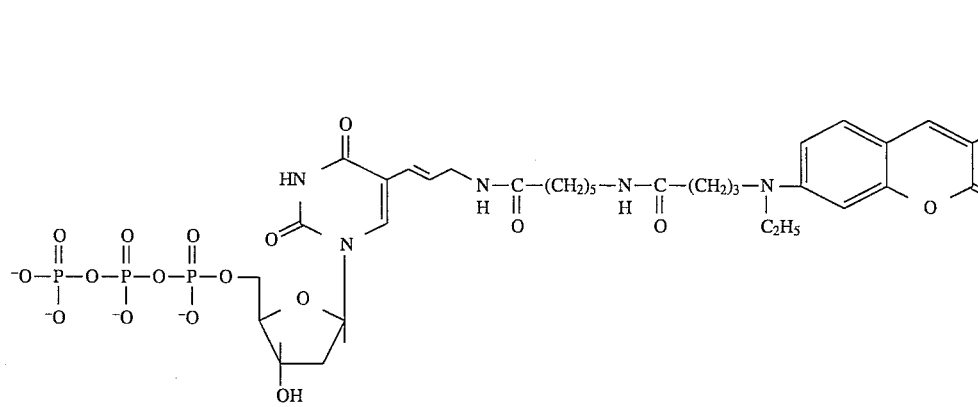

3. The fluorescent label compound according to claim 1 having the formula

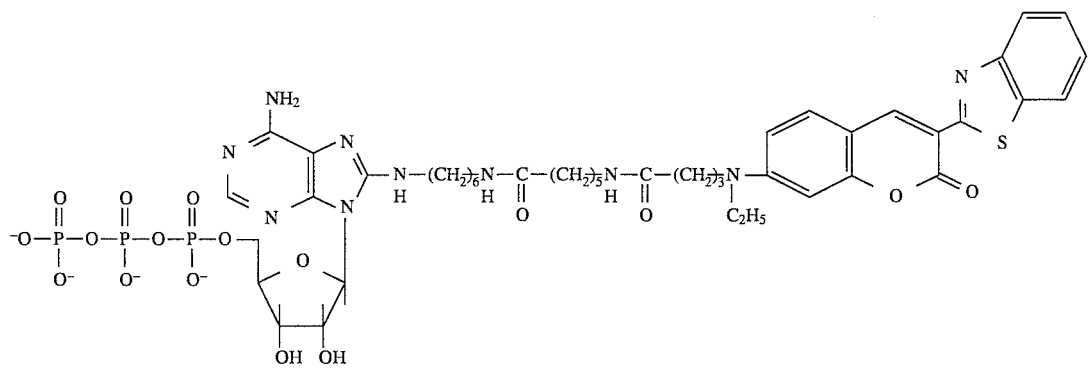

4. In a test for the presence of a particular nucleic acid sequence in a sample, wherein the sample is subjected to a labeled probe under hybridizing conditions and the sample is thereafter assayed for hybridization product, the improvement wherein the probe is labeled with a fluorescent label compound according to claim 1.

5. A diagnostic kit for use in detecting the presence of a particular nucleic acid sequence in a sample, said kit comprising a fluorescent label compound according to claim 1.

* * * * *

UNITED STATES PATENT AND TRADEMARK OFFICE
CERTIFICATE OF CORRECTION

PATENT NO. : 5,587,472
DATED : December 24, 1996
INVENTOR(S) : Dattagupta, et al.

It is certified that error appears in the above-indentified patent and that said Letters Patent is hereby corrected as shown below:

Col. 20, line 49  After " fluorescent " insert
-- label --

Signed and Sealed this

Second Day of December, 1997

Attest:

BRUCE LEHMAN

*Attesting Officer*  *Commissioner of Patents and Trademarks*

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
( A ) LENGTH: 18 nucleotides
( B ) TYPE: Nucleic Acid
( C ) STRANDEDNESS: Single
( D ) TOPOLOGY: Linear ( i i ) MOLECULE TYPE: Other nucleic acid ( x i ) SEQUENCE DESCRIPTION: SEQ ID NO:1:

CTCTATTGAT TACCATGA                                                      18

( 2 ) INFORMATION FOR SEQ ID NO: 2:

( i ) SEQUENCE CHARACTERISTICS:
( A ) LENGTH: 69 nucleotides
( B ) TYPE: Nucleic Acid
( C ) STRANDEDNESS: Single
( D ) TOPOLOGY: Linear ( i i ) MOLECULE TYPE: Other nucleic acid ( x i ) SEQUENCE DESCRIPTION: SEQ ID NO:2:

AGATTTTCTA GATTTCATCT TCCTCCCTAT AGTGAGTCGT ATTATTTTT            50

TTAATACGAC TCACTATAG                                             69